(12) United States Patent
Lindberg et al.

(10) Patent No.: US 7,521,243 B2
(45) Date of Patent: Apr. 21, 2009

(54) ENUMERATION OF WHITE BLOOD CELLS

(75) Inventors: Stellan Lindberg, Förslöv (SE); Johnny Svensson, Ängelholm (SE)

(73) Assignee: Hemocue AB, Ängelholm (SE)

( * ) Notice: Subject to any disclaimer, the term of this patent is extended or adjusted under 35 U.S.C. 154(b) by 723 days.

(21) Appl. No.: 11/102,837

(22) Filed: Apr. 11, 2005

(65) Prior Publication Data

US 2006/0210428 A1    Sep. 21, 2006

(30) Foreign Application Priority Data

Mar. 11, 2005    (SE) .................................... 0500549

(51) Int. Cl.
  *G01N 31/00*    (2006.01)
(52) U.S. Cl. .......................................... 436/10; 422/57
(58) Field of Classification Search .................... 436/10; 422/57
  See application file for complete search history.

(56) References Cited

U.S. PATENT DOCUMENTS

| | | | |
|---|---|---|---|
| 3,824,393 A | | 7/1974 | Brain |
| 4,088,448 A | * | 5/1978 | Lilja et al. .................. 422/102 |
| 4,156,570 A | | 5/1979 | Wardlaw |
| 4,420,558 A | | 12/1983 | De Mey et al. |
| 4,581,223 A | | 4/1986 | Kass |
| 5,188,935 A | * | 2/1993 | Leif et al. .................. 435/7.24 |
| 5,262,302 A | | 11/1993 | Russell |
| 5,472,671 A | | 12/1995 | Nilsson et al. |
| 5,585,246 A | | 12/1996 | Dubrow et al. |
| 5,674,457 A | | 10/1997 | Williamsson et al. |
| 5,874,310 A | | 2/1999 | Li et al. |
| 6,468,807 B1 | | 10/2002 | Svensson et al. |
| 6,552,784 B1 | * | 4/2003 | Dietz et al. .................. 356/246 |

(Continued)

FOREIGN PATENT DOCUMENTS

EP    0 321 889 A2    6/1989

(Continued)

OTHER PUBLICATIONS

Donat-P. Häder, "Novel Method to Determine Vertical Distributions of Phytoplankton in Marine Water Columns", Environmental and Experimental Botany, vol. 35, No. 4, pp. 547 to 555 (1995).

*Primary Examiner*—Jill Warden
*Assistant Examiner*—Rebecca Fritchman
(74) *Attorney, Agent, or Firm*—Buchanan Ingersoll & Rooney, PC

(57) ABSTRACT

A sample acquiring device for volumetric enumeration of white blood cells in a blood sample that includes a measurement cavity for receiving a blood sample. The measurement cavity has a predetermined fixed thickness. The sample acquiring device also has a reagent, which is arranged in a dried form on a surface defining the measurement cavity. The reagent has a hemolysing agent for lysing red blood cells in the sample and a staining agent for selectively staining white blood cells in the sample. Also, a system with the sample acquiring device and a measurement apparatus. The measurement apparatus has a sample acquiring device holder, a light source, and an imaging system for acquiring a digital image of a magnification of the sample The measurement apparatus also has an image analyzer arranged to analyze the acquired digital image for determining the number of white blood cells in the blood sample.

13 Claims, 3 Drawing Sheets

U.S. PATENT DOCUMENTS

| | | | |
|---|---|---|---|
| 6,828,429 B1 * | 12/2004 | Srivastava et al. | 536/23.1 |
| 7,068,365 B2 | 6/2006 | Hansen et al. | |
| 2003/0133119 A1 * | 7/2003 | Bachur, Jr. | 356/436 |
| 2008/0019584 A1 * | 1/2008 | Lindberg et al. | 382/134 |

FOREIGN PATENT DOCUMENTS

| | | |
|---|---|---|
| EP | 0 321 889 A3 | 6/1989 |
| EP | 1500932 A1 | 1/2005 |
| GB | 2152660 A | 8/1985 |
| JP | 2002-148261 A | 5/2002 |
| WO | 97/02482 | 1/1997 |
| WO | WO 99/45384 | 9/1999 |
| WO | WO 02/057997 | 7/2002 |
| WO | WO 03/069421 | 8/2003 |
| WO | WO 03/104771 | 12/2003 |
| WO | WO 2004/001408 | 12/2003 |
| WO | WO 2005/008226 A1 | 1/2005 |

\* cited by examiner

ENUMERATION OF WHITE BLOOD CELLS

TECHNICAL FIELD

The present invention relates to a sample acquiring device, a method and a system for volumetric enumeration of white blood cells in a blood sample.

BACKGROUND OF THE INVENTION

Determining a white blood cell count is often important in connection to treating a patient. This analysis may be needed for diagnosing e.g. leukemia, or infectious or inflammatory diseases or for monitoring treatments. It is desirable to enable analysis results to be obtained as quickly as possible in order to minimize waiting times for patients and enabling a physician to make a decision of treatment and diagnosis directly when making a first examination of the patient. It would therefore be preferable to provide an analysis method which may be quickly performed by the physician or a nurse without the need of sending a test away to a laboratory.

Today, a white blood cell count is normally obtained by staining a blood sample and microscopically viewing the sample in a special counting chamber, e.g. a Bürker chamber. The counting chamber is provided with a grid dividing the chamber in well-defined small volumes. The white blood cell count can then be determined by counting the number of blood cells per box in the grid. The white blood cell count is obtained manually by an analyst, who needs to be experienced in performing the analysis in order to be able to perform a reliable analysis.

This analysis is time-consuming. Further, since it is performed manually, the results of the analysis may vary depending on the person performing the analysis.

There are a few number of existing automated analysis methods for determining a white blood cell count. The white blood cell count may be determined by means of the Coulter principle, which is based on determining cell size and thereby the cell type by sensing an impedance. A method for counting white blood cells by the Coulter principle is described in U.S. Pat. No. 5,262,302.

Another method for determining a white blood cell count is disclosed in U.S. Pat. No. 5,585,246. Here, a blood sample has to be prepared by being mixed with a fluorescent dye and ligand complex which tags the white blood cells. The sample is introduced into a capillary and is irradiated by a laser source which scans over the sample in the capillary. The fluorescence is measured in order to determine the number of white blood cells.

In WO 99/45384, a sample containing chamber having varying thickness is shown. The varying thickness separates different compounds of blood. The blood sample is stained with a colorant to differentially highlight at least three different white blood cell types in the blood sample. The white blood cells may be enumerated by using an optical scanning instrument to view a portion of the chamber.

There is still a need to speed up and simplify existing automated methods for determining a white blood cell count such that analysis may be provided at point of care.

SUMMARY OF THE INVENTION

It is an object of the invention to provide a simple analysis for determining a volumetric enumeration of white blood cells. It is a further object of the invention to provide a quick analysis without the need for complicated apparatuses or extensive sample preparations.

These objects are partly or wholly achieved by a sample acquiring device, a method and a system according to the independent claims. Preferred embodiments are evident from the dependent claims.

Thus, there is provided a sample acquiring device for volumetric enumeration of white blood cells in a blood sample. The sample acquiring device comprises a measurement cavity for receiving a blood sample. The measurement cavity has a predetermined fixed thickness. The sample acquiring device further comprises a reagent, which is arranged in a dried form on a surface defining the measurement cavity, said reagent comprising a hemolysing agent for lysing red blood cells in the blood sample, and a staining agent for selectively staining white blood cells in the blood sample.

The sample acquiring device provides a possibility to directly obtain a sample of whole blood into the measurement cavity and provide it for analysis. There is no need for sample preparation. In fact, the blood sample may be sucked into the measurement cavity directly from a pricked finger of a patient. Providing the sample acquiring device with a reagent enables a reaction within the sample acquiring device which makes the sample ready for analysis. The reaction is initiated when the blood sample comes into contact with the reagent. Thus, there is no need for manually preparing the sample, which makes the analysis especially suitable to be performed directly in an examination room while the patient is waiting.

Whereas many existing methods are able to count different blood cells and even subgroups of blood cells, the sample acquiring device according to the invention is specifically adapted to performing volumetric enumeration of white blood cells. The reagent comprises a hemolysing agent which will lyse the red blood cells in the blood sample. This destroys the possibilities to enumerate the red blood cells in the sample. On the other hand, the lysing of the red blood cells simplifies the distinguishing and identification of the white blood cells within the blood sample.

The invention also provides a method for volumetric enumeration of white blood cells in a blood sample. The method comprises acquiring a blood sample into a measurement cavity of a sample acquiring device, said measurement cavity holding a reagent comprising a hemolysing agent and a staining agent to react with the sample such that the white blood cells are stained, irradiating the sample with the stained white blood cells, acquiring a digital image of a magnification of the irradiated sample in the measurement cavity, wherein white blood cells are distinguished by selective staining of the staining agent, and digitally analysing the digital image for identifying white blood cells and determining the number of white blood cells in the sample.

The invention further provides a system for volumetric enumeration of white blood cells in a blood sample. The system comprises a sample acquiring device as described above. The system further comprises a measurement apparatus comprising a sample acquiring device holder arranged to receive the sample acquiring device which holds a blood sample in the measurement cavity, and a light source arranged to irradiate the blood sample. The measurement apparatus further comprises an imaging system, comprising a magnifying system and a digital image acquiring means for acquiring a digital image of a magnification of the irradiated sample in the measurement cavity, wherein white blood cells are distinguished in the digital image by selective staining of the staining agent. The measurement apparatus also comprises an image analyser arranged to analyse the acquired digital image for identifying white blood cells and determining the number of white blood cells in the blood sample.

The method and system of the invention provide a very simple analysis of a blood sample for determining a white blood cell count. The analysis does not require complicated measurement apparatus or advanced steps to be performed by an operator. Therefore, it may be performed in direct connection to examination of a patient, without the need for a qualified technician. The measurement apparatus utilizes the properties of the sample acquiring device for making an analysis on a sample of undiluted whole blood that has been directly acquired into the measurement cavity. The measurement apparatus is arranged to image a volume of the sample for making a volumetric enumeration of the white blood cells from the one image.

The blood sample is allowed to be mixed with the reagent in the measurement cavity. Within a few minutes, the reaction of the blood sample with the reagent will have hemolysed the red blood cells and stained the white blood cells such that the sample is ready for being presented to the optical measurement. The blood sample may be mixed with the reagent by e.g. dispersion or diffusion of the reagent into the blood sample or by actively vibrating or moving the sample acquiring device so that an agitation is caused in the measurement cavity.

The sample acquiring device may comprise a body member having two planar surfaces to define said measurement cavity. The planar surfaces may be arranged at a predetermined distance from one another to determine a sample thickness for an optical measurement. This implies that the sample acquiring device provides a well-defined thickness to the optical measurement, which may be used for accurately determining the white blood cell count per volumetric unit of the blood sample. A volume of an analysed sample will be well-defined by the thickness of the measurement cavity and an area of the sample being imaged. Thus, the well-defined volume could be used for associating the number of white blood cells to the volume of the blood sample such that the volumetric white blood cell count is determined.

The measurement cavity preferably has a uniform thickness of 50-200 micrometers, and more preferably 100-150 micrometers. This implies that the measurement cavity does not force the blood sample to be smeared into a monolayer allowing a larger volume of blood to be analysed over a small cross-sectional area. Thus, a sufficiently large volume of the blood sample in order to give reliable values of the white blood cell count may be analysed using a relatively small image of the blood sample. For most samples, the white blood cell count is so low that there will be only minor deviations due to white blood cells being arranged on top of each other.

The digital image may be acquired with a depth of field at least corresponding to a third of the thickness of the measurement cavity. If the focus of the imaging system is centered within the thickness of the measurement cavity, the depth of field will be arranged such that the entire thickness of the measurement cavity may be imaged with a sufficient sharpness in order to identify the white blood cells. This implies that a sufficient focus is obtained of the entire sample thickness such that the entire thickness of the measurement cavity may be simultaneously analysed in the digital image of the sample. By choosing not to focus very sharply on a specific part of the sample, a sufficient focus is obtained of the entire sample thickness to allow identifying the number of white blood cells in the sample. The depth of field would more preferably correspond to at least half the thickness of the measurement cavity or even at least the entire thickness of the measurement cavity. This would further facilitate the possibilities of identifying the white blood cells in the blood sample.

The staining agent may be arranged to selectively stain the nucleus of the white blood cells. This implies that the white blood cells may be identified as coloured dots and therefore easily be counted in a digital image.

The staining agent may be any one in the group of Hematoxylin, Methylene blue, Methylene green, Toluidine blue, Gentian violet, Sudan analogues, Gallocyanine, and Fuchsin analogues. However, it should be appreciated that the staining agent is not limited to this group, but many other substances may be contemplated.

The hemolysing agent may be a quaternary ammonium salt, a saponin, a bile acid, such as deoxycholate, a digitoxin, a snake venom, a glucopyranoside or a non-ionic detergent of type Triton. However, it should be appreciated that the hemolysing agent is not limited to this group, but many other substances may be contemplated.

The sample acquiring device may further comprise a sample inlet communicating the measurement cavity with the exterior of the sample acquiring device, said inlet being arranged to acquire a blood sample. The sample inlet may be arranged to draw up a blood sample by a capillary force and the measurement cavity may further draw blood from the inlet into the cavity. As a result, the blood sample may easily be acquired into the measurement cavity by simply moving the sample inlet into contact with blood. Then, the capillary forces of the sample inlet and the measurement cavity will draw up a well-defined amount of blood into the measurement cavity. Alternatively, the blood sample may be sucked or pushed into the measurement cavity by means of applying an external pumping force to the sample acquiring device.

The sample may be irradiated by light of a wavelength corresponding to a peak in absorbance of the staining agent. Consequently, the stained white blood cells which contain an accumulation of staining agent will be detected by a low transmittance of light.

The irradiating may be performed by means of a laser source. The laser source may provide light of a well-defined wavelength fitting the absorbance of the staining agent. Further, the laser source provides collimated light, minimizing disturbances of stray light, such that a point of low transmittance of light will be sharply distinguished.

The irradiating may alternatively be performed by means of a light emitting diode. This light source may still provide sufficient irradiating conditions for properly distinguishing white blood cells from other matter in the sample.

The digital image may be acquired using a magnification power of 10-200×, more preferably 40-100×. Within these ranges of magnification power, the white blood cells are sufficiently magnified in order to be detected, while the depth of field may be arranged to cover the sample thickness.

The analysing comprises identifying areas of high light absorbance in the digital image. The analysing may further comprise identifying black or dark dots in the digital image. Since the staining agents may be accumulated in the nucleus of the white blood cells, the absorbance of the light may have peaks at separate points. These points will form black dots in the digital image.

The analysing may further comprise electronically magnifying the acquired digital image. While the sample is being magnified for acquiring a magnified digital image of the sample, the acquired digital image itself may be electronically magnified for simplifying distinguishing between objects that are imaged very closely to each other in the acquired digital image.

BRIEF DESCRIPTION OF DRAWINGS

The invention will now be described in further detail by way of example under reference to the accompanying drawings.

DETAILED DESCRIPTION OF A PREFERRED EMBODIMENT

Figure 1:
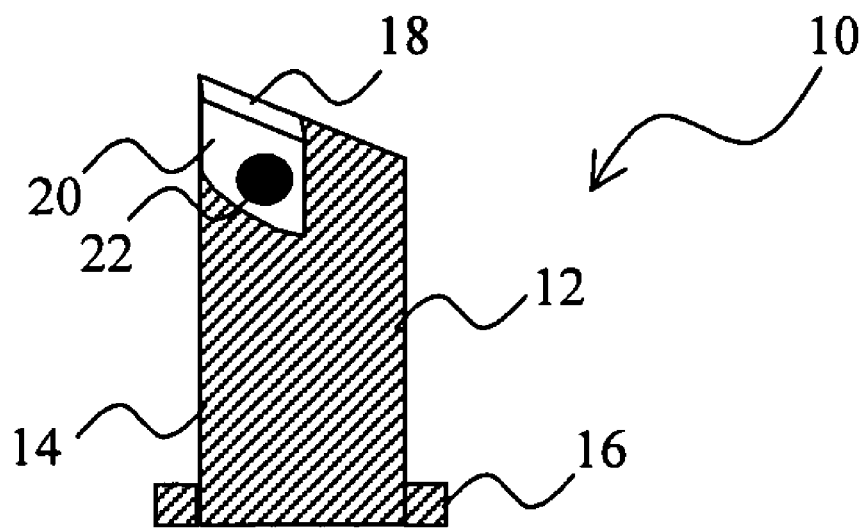
FIG. 1 is a schematic view of a sample acquiring device in the form of a cuvette according to an embodiment of the invention.

Referring now to FIG. 1, a sample acquiring device in the form of a cuvette 10 according to an embodiment of the invention will be described. The cuvette 10 is disposable and is to be thrown away after having been used for analysis. This implies that the cuvette 10 does not require complicated handling. The cuvette 10 is preferably formed in a plastic material and may be manufactured by injection-moulding. This makes manufacture of the cuvette 10 simple and cheap, whereby the costs of the cuvette 10 may be kept down.

The cuvette 10 comprises a body member 12, which has a base 14, which may be touched by an operator without causing any interference in analysis results. The base 14 may also have projections 16 that may fit a cuvette holder in an analysis apparatus. The projections 16 may be arranged such that the cuvette 10 will be correctly positioned in the analysis apparatus.

The cuvette 10 further comprises a sample inlet 18. The sample inlet 18 is defined between opposite walls within the cuvette 10, the walls being arranged so close to each other that a capillary force may be created in the sample inlet 18. The sample inlet 18 communicates with the exterior of the cuvette 10 for allowing blood to be drawn into the cuvette 10. The cuvette 10 further comprises a measurement cavity 20 arranged between opposite walls inside the cuvette 10. The measurement cavity 20 is arranged in communication with the sample inlet 18. The walls defining the measurement cavity 20 are arranged closer together than the walls of the sample inlet 18, such that a capillary force may draw blood from the sample inlet 18 into the measurement cavity 20.

The walls of the measurement cavity 20 are arranged at a distance from each other of 50-200 micrometers, and more preferably 100-150 micrometers. The distance is uniform over the entire measurement cavity 20. The thickness of the measurement cavity 20 defines the volume of blood being examined. Since the analysis result is to be compared to the volume of the blood sample being examined, the thickness of the measurement cavity 20 needs to be very accurate, i.e. only very small variations in the thickness are allowed within the measurement cavity 20 and between measurement cavities 20 of different cuvettes 10. The thickness allows a relatively large sample volume to be analysed in a small area of the cavity. The thickness theoretically allows white blood cells to be arranged on top of each other within the measurement cavity 20. However, the amount of white blood cells within blood is so low that the probability for this to occur is very low.

A surface of a wall of the measurement cavity 20 is at least partly coated with a reagent 22. The reagent 22 may be freeze-dried, heat-dried or vacuum-dried and applied to the surface of the measurement cavity 20. When a blood sample is acquired into the measurement cavity 20, the blood will make contact with the dried reagent 22 and initiate a reaction between the reagent 22 and the blood.

The reagent 22 is applied by inserting the reagent 22 into the measurement cavity 20 using a pipette or dispenser. The reagent 22 is solved in water or an organic solvent when inserted into the measurement cavity 20. The solvent with the reagent 22 may fill the measurement cavity 20. Then, drying is performed such that the solvent will be evaporated and the reagent 22 will be attached to the surfaces of the measurement cavity 20.

The reagent 22 comprises a hemolysing agent and a staining agent. The hemolysing agent may be a quaternary ammonium salt, a saponin, a bile acid, such as deoxycholate, a digitoxin, a snake venom, a glucopyranoside or a non-ionic detergent of type Triton. The staining agent may be Hematoxylin, Methylene blue, Methylene green, Toluidine blue, Gentian violet, a Sudan analogue, Gallocyanine, or a Fuchsin analogue. When a blood sample makes contact with the reagent 22, the hemolysing agent will act to lyse the red blood cells such that the red blood cells are mixed with the blood plasma. Further, the staining agent will accumulate in the nuclei of the white blood cells. The reagent 22 should contain sufficient amounts of staining agent to distinctly stain all the nuclei of the white blood cells. Thus, there will often be a surplus of staining agent, which will be intermixed in the blood plasma. The surplus of staining agent will give a homogenous, low background level of staining agent in the blood plasma. The accumulated staining agent in the white blood cells will be distinguishable over the background level of staining agent.

The reagent 22 may also comprise other constituents, which may be active, i.e. taking part in the chemical reaction with the blood sample, or non-active, i.e. not taking part in the chemical reaction with the blood sample. The active constituents may e.g. be arranged to catalyse the hemolysing or staining action. The non-active constituents may e.g. be arranged to improve attachment of the reagent 22 to the surface of a wall of the measurement cavity 20.

Within a few minutes, the blood sample will have reacted with the reagent 22, such that the red blood cells have been lysed and the staining agent has accumulated in the nuclei of the white blood cells.

Figure 2:
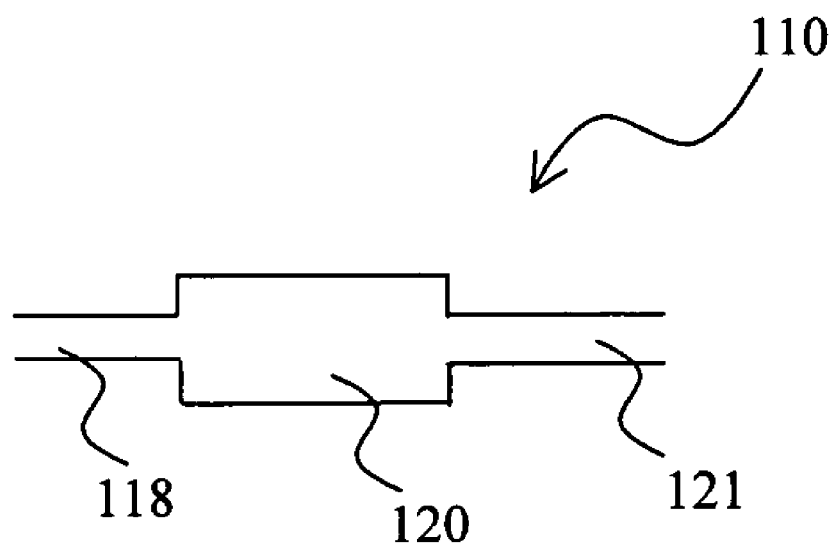
FIG. 2 is a schematic view of a sample acquiring device according to another embodiment of the invention.

Referring to FIG. 2, another embodiment of the sample acquiring device will be described. The sample acquiring device 110 comprises a chamber 120 forming the measurement cavity. The sample acquiring device 110 has an inlet 118 into the chamber 120 for transporting blood into the chamber 120. The chamber 120 is connected to a pump (not shown) via a suction tube 121. The pump may apply a suction force in the chamber 120 via the suction tube 121 such that blood may be sucked into the chamber 120 through the inlet 118. The sample acquiring device 110 may be disconnected from the pump before measurement is performed. Like the measurement cavity of the cuvette, the chamber 120 has a well-defined thickness defining the thickness of the sample to be examined. Further, a reagent 122 is applied to walls of the chamber 120 for reacting with the blood sample.

Figure 3:
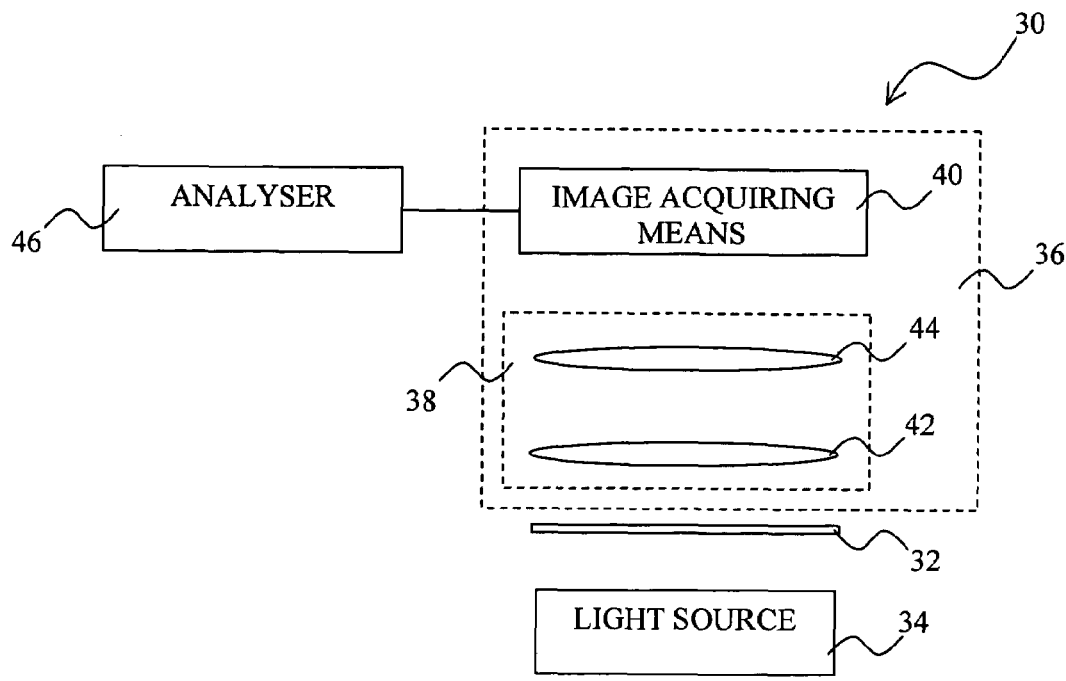
FIG. 3 is a schematic view of a measurement apparatus according to an embodiment of the invention.

Referring now to FIG. 3, an apparatus 30 for volumetric enumeration of white blood cells will be described. The apparatus 30 comprises a sample holder 32 for receiving a cuvette 10 with a blood sample. The sample holder 32 is arranged to receive the cuvette 10 such that the measurement cavity 20 of the cuvette 10 is correctly positioned within the apparatus 30. The apparatus 30 comprises a light source 34 for illuminating the blood sample within the cuvette 10. The light source 34 may be an incandescent lamp, which irradiates light in the entire visible spectrum. The staining agent which is accumulated in the nuclei of the white blood cells will absorb light of specific wavelengths, such that the nuclei of the white blood cells will emerge in a digital image of the sample. If a colour image is acquired, the white blood cells will emerge as specifically coloured dots. If a black and white image is acquired, the white blood cells will emerge as dark dots against a lighter background.

The light source 34 may alternatively be a laser or a light emitting diode. This may be used for increasing contrast in the image such that the white blood cells may be more easily detected. In this case, the light source 34 is arranged to radiate electromagnetic radiation of a wavelength that corresponds to an absorption peak of the staining agent. The wavelength should further be chosen such that the absorption of the blood compounds is relatively low. Further, the cuvette walls should be essentially transparent to the wavelength. For example, where Methylene blue is used as the staining agent, the light source 34 may be arranged to irradiate light having a wavelength of 667 nm.

The apparatus 30 further comprises an imaging system 36, which is arranged on an opposite side of the sample holder 32 relative to the light source 34. Thus, the imaging system 36 is arranged to receive radiation which has been transmitted through the blood sample. The imaging system 36 comprises a magnifying system 38 and an image acquiring means 40. The magnifying system 38 is arranged to provide a magnifying power of 10-200×, more preferably 40-100×. Within these ranges of magnifying power, it is possible to distinguish the white blood cells. Further, the depth of field of the magnifying system 38 may still be arranged to at least correspond to the thickness of the measurement cavity 20.

The magnifying system 38 comprises an objective lens or lens system 42, which is arranged close to the sample holder 32, and an ocular lens or lens system 44, which is arranged at a distance from the objective lens 42. The objective lens 42 provides a first magnification of the sample, which is further magnified by the ocular lens 44. The magnifying system 38 may comprise further lenses for accomplishing an appropriate magnification and imaging of the sample. The magnifying system 38 is arranged such that the sample in the measurement cavity 20 when placed in the sample holder 32 will be focussed onto an image plane of the image acquiring means 40.

The image acquiring means 40 is arranged to acquire a digital image of the sample. The image acquiring means 40 may be any kind of digital camera, such as a CCD-camera. The pixel size of the digital camera sets a restriction on the imaging system 36 such that the circle of confusion in the image plane may not exceed the pixel size within the depth of field. The digital camera 40 will acquire a digital image of the sample in the measurement cavity 20, wherein the entire sample thickness is sufficiently focussed in the digital image for counting the white blood cells. The imaging system 36 will define an area of the measurement cavity 20, which will be imaged in the digital image. The area being imaged together with the thickness of the measurement cavity 20 defines the volume of the sample being imaged. The imaging system 36 is set up to fit imaging blood samples in cuvettes 10. There is no need to change the setup of the imaging system 36. Preferably, the imaging system 36 is arranged within a housing such that the setup is not accidentally changed.

The apparatus 30 further comprises an image analyser 46. The image analyser 46 is connected to the digital camera 40 for receiving digital images acquired by the digital camera 40. The image analyser 46 is arranged to identify patterns in the digital image that correspond to a white blood cell for counting the number of white blood cells being present in the digital image. Thus, the image analyser 46 may be arranged to identify dark dots in a lighter background. The image analyser 46 may be arranged to first electronically magnify the digital image before analysing the digital image. This implies that the image analyser 46 may be able to more easily distinguish white blood cells that are imaged closely to each other, even though the electronic magnifying of the digital image will make the digital image somewhat blurred.

The image analyser 46 may calculate the number of white blood cells per volume of blood by dividing the number of white blood cells being identified in the digital image with the volume of the blood sample, which is well-defined as described above. The volumetric white blood cell count may be presented on a display of the apparatus 30.

The image analyser 46 may be realised as a processing unit, which comprises codes for performing the image analysis.

Figure 4:
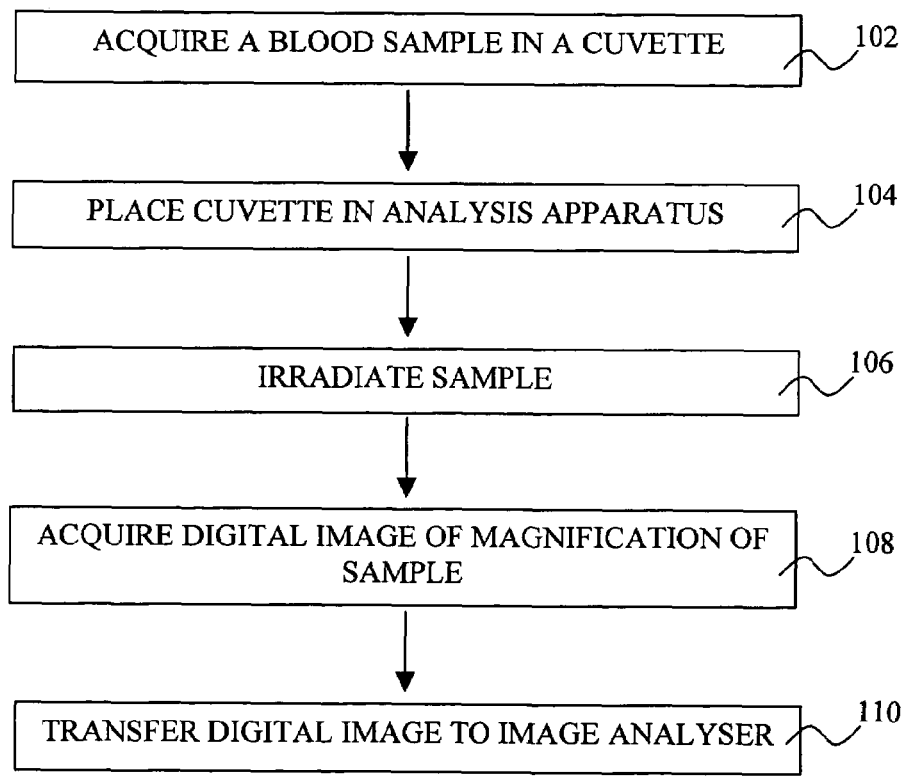
FIG. 4 is a flow chart of a method according to an embodiment of the invention.

Referring to FIG. 4, a method for volumetric enumeration of white blood cells will be described. The method comprises acquiring a blood sample in a cuvette, step 102. An undiluted sample of whole blood is acquired in the cuvette. The sample may be acquired from capillary blood or venous blood. A sample of capillary blood may be drawn into the measurement cavity directly from a pricked finger of a patient. The blood sample makes contact with a reagent in the cuvette initiating a reaction. The red blood cells will be lysed and a staining agent is accumulated in the nuclei of the white blood cells. Within a few minutes from acquiring the blood sample, the sample is ready to be analysed. The cuvette is placed in an analysis apparatus, step 104. An analysis may be initiated by pushing a button of the analysis apparatus. Alternatively, the analysis is automatically initiated by the apparatus detecting the presence of the cuvette.

The sample is irradiated, step 106, and a digital image of a magnification of the sample is acquired, step 108. The sample is being irradiated with electromagnetic radiation of a wavelength corresponding to an absorption peak of the staining agent. This implies that the digital image will contain black or darker dots in the positions of the white blood cell nuclei.

The acquired digital image is transferred to an image analyser, which performs image analysis, step 110, in order to count the number of black dots in the digital image.

Figure 5:
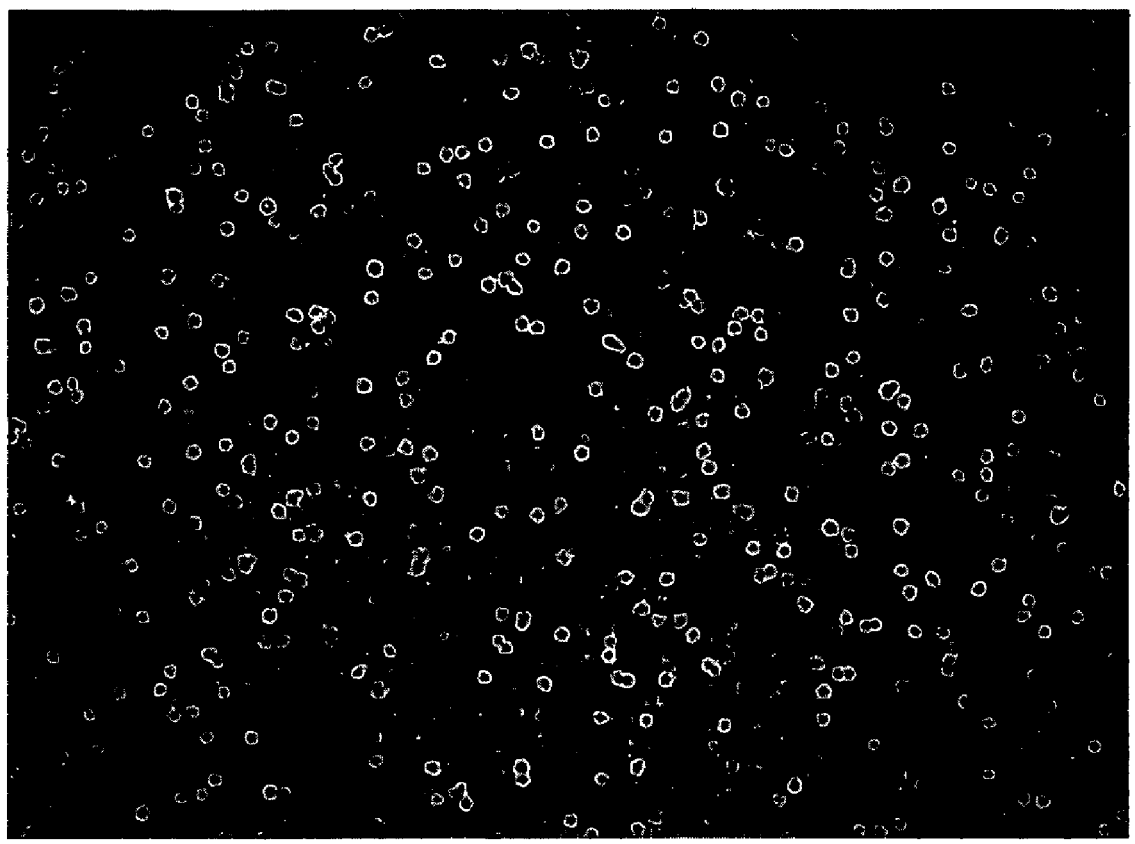
FIG. 5 is a digital image of a blood sample to be used for volumetric enumeration of white blood cells.

In FIG. 5, an example of a digital image is shown to indicate the possibility to identify white blood cells in a blood sample which is hemolysed and stained. This digital image was obtained of a cuvette having a cavity thickness of 140 μm and using 50 times magnification. The light source irradiates white light, indicating that the white blood cells may be identified even though the irradiation is not specifically adapted to an absorption peak of the staining agent. The staining agent used was Methylene blue. Distinct black dots appear in FIG. 5 indicating white blood cells. The image shown in FIG. 5 is a black and white version of a colour image. The contrast between the white blood cells and the background appears clearer in the colour image than in the black and white image reproduced here. The black dots may easily be counted by an image analyser.

In manual methods of counting white blood cells, approximately 200 cells are typically counted for determining the white blood cell count of the blood sample. The method and apparatus presented here may for example be arranged to count approximately 2000 cells, which gives better statistical certainty of the obtained results. A normal, healthy adult has a white blood cell count of 4-5×10$^9$ cells/liter blood. This implies that 2000 cells are found in samples having a volume of 0.4-0.5 µl. For example, if an area of 1.5×1.5 mm in the measurement cavity having a thickness of 140 µm is imaged, the volume being imaged is 0.315 µl. A part of the acquired image may be selected for analysis. Thus, the acquired image may first be coarsely analysed such that no anomalies are allowed in the part being used for determining the white blood cell count. The part of the acquired imaged selected for analysis may be selected having an appropriate size so that a sufficient volume of the blood sample will be analysed.

It should be emphasized that the preferred embodiments described herein is in no way limiting and that many alternative embodiments are possible within the scope of protection defined by the appended claims.

The invention claimed is:

1. A method for volumetric enumeration of white blood cells in a blood sample, said method comprising:
   acquiring a blood sample into a measurement cavity of a sample acquiring device, said measurement cavity holding a reagent comprising a hemolysing agent and a staining agent to react with the sample such that the white blood cells are stained,
   irradiating the sample with the stained white blood cells,
   acquiring a digital image of a magnification of the irradiated sample in the measurement cavity, wherein white blood cells are distinguished by selective staining of the staining agent, and
   digitally analyzing the digital image for identifying white blood cells and determining the number of white blood cells in the samples,
   wherein said digital image is acquired with a depth of field at least corresponding to a third of the thickness of the measurement cavity.

2. The method according to claim 1, wherein the blood sample is mixed with the reagent in the measurement cavity.

3. The method according to claim 2, wherein the measurement cavity has a thickness of 50-200 micrometers.

4. The method according to claim 3, wherein a volume of an analysed sample is well-defined by the thickness of the measurement cavity and an area of the sample being imaged.

5. The method according to claim 1, wherein the sample is irradiated by light of a wavelength corresponding to a peak in absorbance of the staining agent.

6. The method according to claim 1, wherein said irradiating is performed by means of a laser source.

7. The method according to claim 1, wherein said irradiating is performed by means of a light emitting diode.

8. The method according to claim 1, wherein the digital image is acquired using a magnification power of 10-200×.

9. The method according to claim 1, wherein said analysing comprises identifying areas of high light absorbance in the digital image.

10. The method according to claim 9, wherein said analysing comprises identifying black dots in the digital image.

11. The method according to claim 1, wherein said analysing comprises electronically magnifying the acquired digital image.

12. The method according to claim 2, wherein the measurement cavity has a thickness of 100-150 micrometers, and said digital image is acquired with a depth of field at least corresponding to a third of the thickness of the measurement cavity.

13. The method according to claim 1, wherein the digital image is acquired using a magnification power of 40-100×.

* * * * *